(12) United States Patent
Van Den Berg et al.

(10) Patent No.: US 7,456,212 B2
(45) Date of Patent: Nov. 25, 2008

(54) STORAGE STABLE CYCLIC KETONE PEROXIDE COMPOSITIONS

(75) Inventors: Rolf Hendrik Van Den Berg, Kring van Dorth (NL); Bart Fischer, Leusden (NL); Frans Johannes Hoogesteger, Nijmegen (NL); Simon Put, Velp (NL)

(73) Assignee: Akzo Nobel N.V., Arnhem (NL)

( * ) Notice: Subject to any disclaimer, the term of this patent is extended or adjusted under 35 U.S.C. 154(b) by 368 days.

(21) Appl. No.: 10/543,606

(22) PCT Filed: Jan. 28, 2004
(Under 37 CFR 1.47)

(86) PCT No.: PCT/EP2004/000743

§ 371 (c)(1),
(2), (4) Date: Jul. 28, 2005

(87) PCT Pub. No.: WO2004/072059

PCT Pub. Date: Aug. 26, 2004

(65) Prior Publication Data
US 2006/0281881 A1  Dec. 14, 2006

Related U.S. Application Data

(60) Provisional application No. 60/447,177, filed on Feb. 13, 2003.

(30) Foreign Application Priority Data

Oct. 13, 2003  (EP)  .................................. 03078216

(51) Int. Cl.
*A01N 43/02* (2006.01)
*A61K 31/335* (2006.01)

(52) U.S. Cl. ..................................................... 514/450
(58) Field of Classification Search .................. 514/450
See application file for complete search history.

(56) References Cited

U.S. PATENT DOCUMENTS 5,808,110 A     9/1998  Torenbeek
2001/0034466 A1  10/2001  Deckers et al.

FOREIGN PATENT DOCUMENTS

| EP | 1134237 A | 9/2001 |
|---|---|---|
| EP | 1 186 618 A | 3/2002 |
| EP | 1 279 684 A | 1/2003 |
| JP | 10-087652 A | 4/1998 |
| WO | WO 96/03397 | 2/1996 |
| WO | WO 96-03444 A | 2/1996 |
| WO | 99/32584 * | 7/1999 |
| WO | WO 99/32584 | 7/1999 |
| WO | WO 01 68723 A | 9/2001 |
| WO | WO 2004/052877 | 6/2004 |

OTHER PUBLICATIONS

Oxley et al., Journal of Forensic Sciences, 2001, vol. 46, pp. 1070-1075.*

* cited by examiner

*Primary Examiner*—D. Margaret Seaman
*Assistant Examiner*—Niloofar Rahmani
(74) *Attorney, Agent, or Firm*—Kenyon & Kenyon LLP

(57) ABSTRACT

The present invention relates to peroxide compositions comprising one or more cyclic ketone peroxides, one or more dialkyl peroxides, and, optionally, one or more conventional phlegmatisers. These compositions are safe and storage stable. In addition, the invention also pertains to the use of such compositions in polymerization and (co)polymer modification processes.

15 Claims, No Drawings

STORAGE STABLE CYCLIC KETONE PEROXIDE COMPOSITIONS

This application claims the benefit of U.S. Provisional Application No. 60/447,177, filed Feb. 13, 2003 and European Patent Application No. 03078216.3 filed Oct. 13, 2003. The entire disclosures of the prior applications are hereby incorporated by reference herein in their entireties.

The present invention relates to peroxide compositions comprising one or more crystallizing cyclic ketone peroxides, one or more dialkyl peroxides, and, optionally, one or more conventional phlegmatisers. The present invention also pertains to the use of such compositions in polymerization and (co)polymer modification processes.

U.S. Pat. No. 5,808,110 discloses transportable, storage stable cyclic ketone peroxide compositions, which comprise one or more cyclic ketone peroxides and one or more diluents selected from the group consisting of liquid phlegmatisers for cyclic ketone peroxides, plasticizers, solid polymeric carriers, inorganic supports, organic peroxides, and mixtures thereof. In these compositions at least 20% of the total active oxygen content must be attributable to one or more cyclic ketone peroxides. However, the compositions that are disclosed have such a high active oxygen content of the cyclic ketone peroxides that they impair a safety hazard when stored at −10° C. or below due to the formation of explosive crystals, which results in an explosion when heated and thus impairs an enormous safety hazard.

A solution for this problem of explosive crystals is provided in non-published patent application EP-A-02080128, which discloses a cyclic ketone peroxide composition comprising one or more crystallizing peroxides, optionally one or more conventional phlegmatisers (diluents), and a co-crystallizing compound which solidifies in the final composition at a solidification temperature above the crystallization temperature of the crystallizing peroxide. Although compositions of EP-A-02080128 have many advantageous properties, i.e. they have a high active oxygen content and they are safe and storage stable, these compositions are not suitable for all types of polymerization and (co)polymer modification processes. For example, in the production process of low-density polyethylene (LDPE), the co-crystallizing compound solidifies under the high pressure reaction conditions that are applied, which may block the conduits of the (tubular) reactor system, particularly the peroxide dosing conduits, that is used.

It is not desired to simply dilute the compositions of U.S. Pat. No. 5,808,110, since this results in compositions with a too low active oxygen content. The manufacture of a cyclic ketone peroxide composition with high total active oxygen content is advantageous with respect to efficient use of the reactor and the reagents and to prevent contamination of polymers, produced with these peroxide compositions, with undesired diluent.

Hence, it is an object of the present invention to provide a cyclic ketone peroxide composition comprising one or more crystallizing cyclic ketone peroxides, wherein the composition has a high active oxygen content and, furthermore, has good safety and storage stability. It is another object of the present invention to provide a cyclic ketone peroxide composition that is suitable for use in polymerization and (co)polymer modification processes, even for processes that require increased or high pressure.

The present invention provides a cyclic ketone peroxide composition comprising:

one or more crystallizing cyclic ketone peroxides of formula (I)

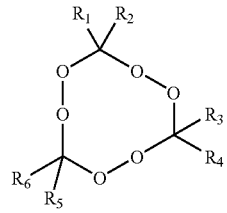

wherein $R_1$-$R_6$ are independently selected from the group consisting of hydrogen, linear or branched $C_1$-$C_{20}$ alkyl, $C_3$-$C_{20}$ cycloalkyl, $C_6$-$C_{20}$ aryl, $C_7$-$C_{20}$ aralkyl and $C_7$-$C_{20}$ alkaryl, and each of $R_1$-$R_6$ may be optionally substituted with one or more groups selected from hydroxy, $C_1$-$C_{20}$ alkoxy, linear or branched $C_1$-$C_{20}$ alkyl, $C_6$-$C_{20}$ aryloxy, halogen, ester, carboxy, nitrile, and amido, one or more dialkyl peroxides according to formula $R_7$—O—O—$R_8$ (II), wherein $R_7$ and $R_8$ are independently selected from the group consisting of substituted or unsubstituted, linear or branched $C_4$-$C_{20}$, $C_3$-$C_{20}$ cycloalkyl, $C_6$-$C_{20}$ aryl, $C_7$-$C_{20}$ aralkyl, and $C_7$-$C_{20}$ alkaryl, and optionally, one or more conventional phlegmatisers (diluents).

The active oxygen content of a peroxide as described in this description is calculated according to the formula: 16×the number of peroxide bonds/molecular weight of the peroxide× 100%. The active oxygen content of a composition is a weighed average of all compounds of the composition.

The term "crystallizing cyclic ketone peroxide" in this description is used for any cyclic ketone peroxide having an active oxygen content of 3.5% or more and optionally diluted with Isopar® M that forms crystals when subjected to the "crystallization test" as described below.

Cyclic ketone peroxide formulations in accordance with the invention do not form explosive crystals when subjected to the "crystallization test" and have sufficiently high active oxygen content to allow a generic use. Furthermore, addition of a seed crystal to the composition of the present invention does not initiate crystal growth of the seeds, nor does it result in the formation of additional crystals, not even at a temperature as low as −25° C., such as applied in the "crystallization test". Particularly preferred is the situation wherein the added seed crystals dissolve in the composition, even at a temperature as low as −25° C. Consequently, compositions according to this invention are safe and storage stable. The terms "storage stable" and "storage stability" used in the description mean that the composition is not liable to explode when stored, or heated after storage, at a minimum storage temperature of −20° C. and a maximum storage temperature that is determined by the maximum storage temperature of the most labile peroxide in the composition. In addition, these compositions are suitable for many kinds of polymerization and (co)polymer modification processes, including processes that require increased or high pressure.

Preferred cyclic ketone peroxides that can be used in a cyclic ketone peroxide composition according to this invention include the cyclic ketone peroxides derived from acetone, acetyl acetone, methyl ethyl ketone, methyl propyl ketone, methyl isopropyl ketone, methyl butyl ketone, methyl isobutyl ketone, methyl amyl ketone, methyl isoamyl ketone, methyl hexyl ketone, methyl heptyl ketone, diethyl ketone, ethyl propyl ketone, ethyl amyl ketone, methyl octyl ketone, methyl nonyl ketone, cyclopentanone, cyclohexanone, 2-methylcyclohexanone, 3,3,5-trimethyl cyclohexanone, and mixtures thereof. More preferred is the use of cyclic ketone peroxides derived from acetone, methyl ethyl ketone, methyl propyl ketone, methyl isopropyl ketone, methyl butyl ketone, methyl isobutyl ketone, methyl amyl ketone, methyl isoamyl ketone, cyclohexanone, and mixtures thereof. The use of cyclic ketone peroxide derived from methyl ethyl ketone, and optionally, further ketones, is most preferred. The preparation of cyclic ketone peroxides from the appropriate ketone generally results in a mixture of peroxides, which predominantly consists of the trimeric and dimeric forms. However, the mixture of peroxides may also comprise some linear as well as some tetrameric and higher oligomeric cyclic structures. The ratio between the various forms, notably the trimer/dimer ratio, mainly depends on the reaction conditions during the preparation, and the person skilled in the art is referred to WO 96/03397 for obvious variations in the reaction conditions that can be carried out in order to influence this ratio. Preferably, the cyclic ketone peroxide consists essentially of trimer and dimer. If so desired, the reaction mixture may be separated into the individual cyclic ketone peroxide compounds. However, in order to avoid laborious purification procedures, the composition of the invention will typically contain some dimeric structures next to trimeric structures, as defined above. Preference for certain compositions or individual compounds may depend on differences in physical properties or requirements in the application of the peroxides, e.g. storage stability, half-life time vs. temperature, volatility, boiling point, solubility, etc.

Preferably, the composition according the invention has a total active oxygen content of more than 3 percent by weight (wt. %), based on the total weight of the composition. Preferably, the composition comprises at most 11 wt. %, more preferably at most 10 wt. %, and most preferably at most 8 wt. % of active oxygen, based on the total weight of the composition. For storing and transporting bulk quantities of composition according to the invention it may be necessary to dilute the composition with a conventional (inert) phlegmatiser, thereby reducing the total active oxygen content of the composition.

Preferably, the composition of the invention comprises at least 1 wt. %, more preferably at least 5 wt. %, and most preferably at least 10 wt. % of the cyclic ketone peroxide, and preferably at most 50 wt. %, more preferably at most 25 wt. %, even more preferably at most 20 wt. %, yet even more preferably at most 17.5 wt. %, and most preferably at most 15 wt. % of the cyclic ketone peroxide, based on the total weight of the composition, preferably such that the active oxygen content attributable to the cyclic ketone peroxide remains below 6 wt. %, preferably below 3.5 wt. %, and most preferably below 3 wt. %, based on the total weight of cyclic ketone peroxide composition.

The dialkyl peroxide of formula $R_7$—O—O—$R_8$ (II) in the composition of the present invention can be any symmetrical or asymmetrical dialkyl peroxide with $R_7$ and $R_8$ as defined above. Preferred are dialkyl peroxides according to formula $R_7$—O—O—$R_8$ (II) wherein $R_7$ and $R_8$ are independently selected from the group consisting of linear or branched $C_4$-$C_{12}$ alkyl moieties and, more preferred wherein at least one of $R_7$ and $R_8$ is selected from the group consisting of branched $C_4$-$C_{12}$ alkyl moieties, even more preferred are dialkyl peroxides according to formula $R_7$—O—O—$R_8$ (II) wherein both $R_7$ and $R_8$ are independently selected from the group consisting of branched $C_4$-$C_{12}$ alkyl moieties. Preferred dialkyl peroxides include di(tert-butyl) peroxide, di(tert-amyl) peroxide, (tert-butyl)(tert-amyl) peroxide, 2,5-dimethyl-2,5-di(tert-butylperoxy)hexane, 2,5-dimethyl-2,5-di(tert-butylperoxy)-3-hexyne, and (1,1,3,3-tetrametylbutyl)(tert-butyl) peroxide, more preferred dialkyl peroxides include di(tert-butyl) peroxide and di(tert-amyl) peroxide, and the most preferred dialkyl peroxide is di(tert-butyl) peroxide. A composition according to the invention preferably comprises at least 10 wt. %, more preferably at least 20 wt. %, even more preferably at least 40 wt. %, yet even more preferably at least 50 wt. %, and most preferably at least 60 wt. % of one or more dialkyl peroxides, and preferably at most 99 wt. %, more preferably at most 95 wt. %, and most preferably at most 90 wt. % of one or more dialkyl peroxides, based on the total weight of the composition.

The conventional phlegmatiser (an inert diluent) that may be optionally added to the composition of this invention can be any conventional phlegmatiser. Also mixtures of one or more of these conventional phlegmatisers may be used. If conventional phlegmatiser is added, then the composition according to the invention preferably comprises at least 1 wt. %, more preferably at least 5 wt. %, and most preferably at least 10 wt. % of one or more conventional phlegmatisers, and preferably at most 99 wt. %, more preferably at most 90 wt. %, and most preferably at most 80 wt. % of the one or more conventional phlegmatisers, based on the total weight of the cyclic ketone peroxide composition. Preferred conventional phlegmatisers for the cyclic ketone peroxides include alkanols, cycloalkanols, alkylene glycols, alkylene glycol monoalkyl ethers, cyclic ether substituted alcohols, cyclic amides, aldehydes, ketones, epoxides, esters, phosphates, hydrocarbon solvents, halogenated hydrocarbon solvents, paraffinic oils, white oils, silicone oils, and mixtures thereof.

Preferred esters which can be used as conventional phlegmatiser in the composition of the present invention include, but are not limited to, monocarboxylic esters of mono- and dihydric alcohols, dicarboxylic acid esters of monohydric alcohols, carbonates of monohydric alcohols, alkoxyalkyl esters, β-keto esters, phthalates, phosphates, benzoates, adipates and citrates. More preferred esters useful as conventional phlegmatiser in compositions of the present invention are selected from the group consisting of dimethyl phthalate, dibutyl phthalate, dioctyl phthalate, dibenzyl phthalate, butyl benzyl phthalate, diallyl phthalate, n-pentyl acetate, isopentyl acetate, n-hexyl acetate, 2-ethylhexyl acetate, benzyl acetate, methyl benzoate, ethyl benzoate, isopropyl benzoate, n-octyl benzoate, isodecyl benzoate, n-butyl pivalate, isoamyl pivalate, sec-amyl pivalate, n-hexyl pivalate, dioctyl adipate, diisodecyl adipate, methyl neodecanoate, n-butyl neodecanoate, propylene glycol diacetate, ethylene glycol diacetate, cyclohexyl acetate, neopentyl acetate, methyl-2-ethylhexanoate, n-heptyl formate, n-octyl formate, dipropyl carbonate, dibutyl carbonate, isoamyl propionate, sec-amyl propionate, benzyl propionate, butyl caproate, ethylene glycol dipropionate, heptyl propionate, methylphenyl acetate, octyl acetate, 2-ethylhexyl acetate, propyl caprylate, methyl decanoate, dimethyl succinate, diethyl succinate, dimethyl malonate, diethyl malonate, methylethyl succinate, diisobutyl nylonate, 2,2,4-trimethyl-1,3-pentanediol, diethyl oxalate, methyl p-toluate, acetyltributyl citrate, and mixtures thereof.

Preferred phosphates which can be used as conventional phlegmatiser in the composition of the present invention include, but are not limited to, triethyl phosphate, tricresyl phosphate, trixylyl phosphate, cresyl diphenyl phosphate, 2-ethylhexyl-diphenyl phosphate, isodecyl-diphenyl phosphate, tri(2-ethylhexyl) phosphate, dimethyl methylphosphonate, chlorinated phosphate esters, tributyl phosphate, tributoxyethyl phosphate, and mixtures thereof.

Preferred linear and branched hydrocarbon solvents which can be used as conventional phlegmatiser in compositions of the present invention include, but are not limited to, hydrogenated oligomers of alkanes such as Isopar® products (ex. Exxon), such as Isopar® M, pentane, heptane, isododecane, amyl benzene, isoamyl benzene, decalin, o-diisopropyl benzene, m-diisopropyl benzene, n-dodecane, 2,4,5,7-tetramethyl octane, n-amyl toluene, 1,2,3,4-tetramethyl benzene, 3,5-diethyl toluene and hexahydronaphthalene, tetradecane, tridecane, Exxsol® D80, Exxsol® D100, Exxsol® D100S, Soltrol® 145, Soltrol® 170, Varsol® 80, Varsol® 110, Shellsol® D100, Shellsol® D70, Halpasol® i 235/265, and mixtures thereof. Particularly preferred conventional phlegmatisers are Isopar® M and Soltrol® 170.

Preferred halogenated hydrocarbons include phenyl trichloride, 3-bromo-o-xylene, 4-bromo-o-xylene, 2-bromo-m-xylene, 4-bromo-m-xylene, 5-bromo-m-xylene, o-dibromobenzene, p-dibromobenzene, 1,4-dibromobutane, 1,1-dibromo-2,2-dichloroethane, bromooctane, tetrabromoethylene, 1,2,3-trichlorobenzene, 1,2,4-trichlorobenzene, and mixtures thereof.

Preferred aldehydes useful as conventional phlegmatiser in compositions of the present invention include n-chlorobenzaldehyde and decanal.

Preferred ketones useful in the compositions of the present invention include acetophenone, isophorone, isobutyl ketone, methylphenyl diketone, diamyl ketone, diisoamyl ketone, ethyloctyl ketone, ethylphenyl ketone, acetone, methyl-n-amyl ketone, ethylbutyl ketone, ethylpropyl ketone, methylisoamyl ketone, methylheptyl ketone, methylhexyl ketone, ethylamyl ketone, dimethyl ketone, diethyl ketone, dipropyl ketone, methylethyl ketone, methylisobutyl ketone, methylisopropyl ketone, methylpropyl ketone, methyl-t-butyl ketone, isobutylheptyl ketone, diisobutyl ketone, 2,4-pentanedione, 2,4-hexanedione, 2,4-heptanedione, 3,5-heptanedione, 3,5-octanedione, 5-methyl-2,4-hexanedione, 2,6-dimethyl-3,5-heptanedione, 2,4-octanedione, 5,5-dimethyl-2,4-hexanedione, 6-methyl-2,4-heptanedione, 1-phenyl-1,3-butanedione, 1-phenyl-1,3-pentanedione, 1,3-diphenyl-1,3-propanedione, 1-phenyl-2,4-pentanedione, methylbenzyl ketone, phenylethyl ketone, methylchloromethyl ketone, methylbromomethyl ketone, 2-pyrrolidone, N-methyl-pyrrolidone, coupling products thereof, and mixtures thereof.

A preferred epoxide which may be employed as conventional phlegmatiser in compositions of the present invention is styrene oxide.

Preferred alcohols useful as conventional phlegmatiser in compositions of the present invention are n-butyl alcohol, capryl alcohol, octyl alcohol, dodecyl alcohol, tetrahydrofurfuryl alcohol, 1,4-dihydroxymethyl cyclohexane, cyclohexanol, glycerol, ethylene glycol, polyethylene glycols with molecular weights under 20,000 g/mol, propylene glycol, dipropylene glycol, neopentyl glycol, hexylene glycol, 1,4-butylene glycol, 2,3-butylene glycol, butene diol, 1,5-pentane diol, 3,6-dimethyloctane-3,6-diol, 2,5-dimethyl-hex-3-yne-2,5-diol, 2,4,7,9-tetramethyldecane-4,7-diol, 2,2,4,4-tetramethyl-1,3-cyclobutanediol, ethylene glycol monoethyl ether, ethylene glycol monobutyl ether, diethylene glycol monoethyl ether, diethylene glycol monobutyl ether, and mixtures thereof.

Preferred paraffinic oils useful as conventional phlegmatiser in composition of the present invention include, but are not limited to, halogenated paraffinic oils and paraffinic diesel oil. Other oils, including white oils, epoxidized soybean oils and silicone oils, are also useful as conventional phlegmatiser in the compositions of the present invention.

The safety of the composition of the present invention was determined by keeping the composition at −25° C. for 48 hours, followed by examination of the composition for the presence of crystals ("crystallization test"). (If no crystals are formed after 24 hours at −25° C., a very small amount of seed crystals of pure cyclic ketone peroxide is added to the composition. After addition of the seed crystals, the composition is set aside for another 24 hours at −25° C. Finally, the composition is examined. The composition is considered safe and stable if:

the seed crystals did not grow (provided that seed crystals were added), no crystals are present or (in case seed crystals were added) no additional crystals are present, or, the composition is completely free of crystals, i.e. even optionally added seed crystals have dissolved.

In addition to the above described "crystallization test", the composition of the present invention should also pass the following conventional safety tests:

Deflagration test (deflagration),

Time Pressure test (deflagration),

Koenen test (heating under defined confinement),

Pressure Vessel test (PVT) (heating under defined confinement), and

Thermal Explosion Vessel test (heating under defined confinement).

Passing these tests means a "medium" or "low" rating in the heating under defined confinement tests and a "no" or "yes, slowly" rating in the deflagration tests. The final hazard rating, for which the most severe rating in any one of the tests is used, must be "medium" or "low." The safety tests and corresponding criteria are documented in the "United Nations Recommendations on the Transport of Dangerous Goods, Manual of Tests and Criteria".

In a preferred embodiment of this invention, the cyclic ketone peroxide is manufactured directly in one or more of the conventional phlegmatisers as described above, followed by combining the cyclic ketone peroxide/conventional phlegmatiser mixture with one or more dialkyl peroxides of formula (II). Optionally, one or more additional conventional phlegmatisers may be added. As already mentioned above, the manufacture of a cyclic ketone peroxide composition with high total active oxygen content is advantageous with respect to efficient use of the reactor and the reagents.

For storing and transporting bulk quantities of the composition according to this invention it may be necessary to (further) dilute the cyclic ketone peroxide composition of the invention with one or more dialkyl peroxides of formula (II) and/or one or more conventional phlegmatisers, such that it complies with regulations for safe storage and transport. This is particularly the case for bulk quantities, which are stored and transported in tanks and intermediate bulk containers (IBCs). The dialkyl peroxide(s) and conventional phlegmatiser(s) are preferably added after the preparation of the cyclic ketone peroxide, as long as it is added before storage. If so desired, conventional phlegmatiser(s) may also be added before or during the preparation of the cyclic ketone peroxide.

It is noted that the dialkyl peroxide of formula (II) and, if used, the conventional phlegmatiser, may be combined before use. Hence, in that case it is feasible to purchase and use specific dialkyl peroxides that contain one or more conventional phlegmatiser.

The composition of the present invention may optionally contain certain additives as long as these additives do not significantly suppress the safety, transportability and/or storage stability of the composition. As examples of such additives are mentioned: antiozonants, antioxidants, anti-degradants, UV stabilizers, coagents, fungicides, antistatic agents, pigments, dyes, coupling agents, dispersing aids, blowing agents, lubricants, process oils, and mould-release agents. These additives may be employed in their usual amounts. If used, such additives are typically added to the cyclic ketone peroxide composition shortly before the composition is used in a polymerization or (co)polymer modification process.

The present invention also relates to the use of cyclic ketone peroxide compositions in (radical) polymerization processes, (co)polymer modification processes, such as controlled rheology polypropylene (CR-PP) processing, and other reactions involving peroxides, like the synthesis of certain chemicals. Compositions according to the present invention are pre-eminently suitable for polymerization or (co) polymer modification processes that require increased or high pressure. As an example is mentioned the high-pressure polymerization process of ethylene to produce low-density polyethylene (LDPE). In the polymerization reactions, conventional additives can be used, such as chain transfer agents and the like.

The present invention is illustrated by the following examples.

Materials:
Di(tert-butyl) peroxide-product (Trigonox® B) ex Akzo Nobel (Assay: 99 wt. %, Active Oxygen: 10.83 wt. %)
Cyclic methyl ethyl ketone peroxide-product (Trigonox® 301) ex Akzo Nobel (Assay: 41% in Isopar® M, Active Oxygen: 7.45 wt. %)

EXAMPLE 1

Preparation of a composition comprising 16.4 percent by weight (wt. %) of cyclic methyl ethyl ketone peroxide, 60 wt. % of di(tert-butyl) peroxide, and 23.6 wt. % of Isopar® M: A reaction vessel is charged with 900 grams of Trigonox® B. Next, 600 grams of Trigonox® 301 is dosed. The obtained mixture has a total active oxygen content of 9.41 wt. % and an active oxygen content attributable to cyclic methyl ethyl ketone peroxide of 2.98 wt. %.

This composition passes the PVT test: Low

EXAMPLE 2

Preparation of a composition comprising 20.5 percent by weight (wt. %) of cyclic methyl ethyl ketone peroxide, 50 wt. % of di(tert-butyl) peroxide, and 29.5 wt. % of Isopar® M: A reaction vessel is charged with 750 grams of Trigonox® B. Next, 750 grams of Trigonox® 301 is dosed. The obtained mixture has a total active oxygen content of 9.14 wt. % and an active oxygen content attributable to cyclic methyl ethyl ketone peroxide of 3.73 wt. %.

This composition passes the PVT test: Low

COMPARATIVE EXAMPLES

The cyclic methyl ethyl ketone peroxide showed formation of crystals when formulated with just Isopar® M such that the product had an active oxygen content of 3.5% or more.

The invention claimed is:

1. A cyclic ketone peroxide polymerization initiator composition comprising:
one or more cyclic ketone peroxides of formula (I)

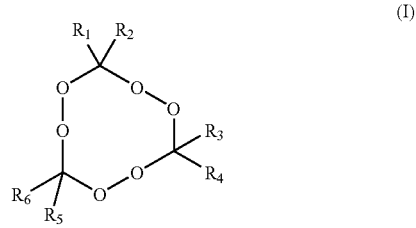

(I)

wherein $R_1$-$R_6$ are independently selected from the group consisting of hydrogen, linear or branched $C_1$-$C_{20}$ alkyl, $C_3$-$C_{20}$ cycloalkyl, $C_6$-$C_{20}$ aryl, $C_7$-$C_{20}$ aralkyl and $C_7$-$C_{20}$ alkaryl, and each of $R_1$-$R_6$ may be optionally substituted with one or more groups selected from hydroxy, $C_1$-$C_{20}$ alkoxy, linear or branched $C_1$-$C_{20}$ alkyl, $C_6$-$C_{20}$ aryloxy, halogen, ester, carboxy, nitrile, and amido, and whereby each of the combination of groups $R_1$ and $R_2$, $R_3$ and $R_4$, and $R_5$ and $R_6$, together with the carbon to which each combination of groups is attached may optionally form a cyclic moiety; and one or more dialkyl peroxides according to formula $R_7$—O—O—$R_8$ (II), wherein $R_7$ and $R_8$ are independently selected from the group consisting of unsubstituted, linear or branched $C_4$-$C_{20}$ alkyl, $C_3$-$C_{20}$ cycloalkyl, $C_6$-$C_{20}$ aryl, $C_7$-$C_{20}$ aralkyl, and $C_7$-$C_{20}$ alkaryl, wherein the composition does not form explosive crystals when stored at $-25°$ C. for 24 hours.

2. A cyclic ketone peroxide polymerization initiator composition comprising: one or more cyclic ketone peroxides of formula (I)

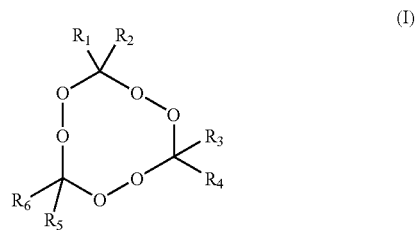

(I)

wherein $R_1$-$R_6$ are independently selected from the group consisting of hydrogen, linear or branched $C_1$-.$C_{20}$ alkyl, $C_3$-$C_{20}$ cycloalkyl, $C_6$-$C_{20}$ aryl, $C_7$-$C_{20}$ aralkyl and $C_7$-$C_{20}$ alkaryl, and each of $R_1$-$R_6$ may be optionally substituted with one or more groups selected from hydroxy, $C_1$-$C_{20}$ alkoxy, linear or branched $C_1$-$C_{20}$ alky 1, $C_6$-$C_{20}$ aryloxy, halogen, ester, carboxy, nitrile, and amido; and one or more dialkyl peroxides according to formula $R_7$—O—O—$R_8$ (II), wherein $R_7$ and $R_8$ are independently selected from the group consisting of unsubstituted, linear or branched $C_4$-$C_{20}$ alkyl, $C_3$-$C_{20}$ cycloalkyl, $C_6$-$C_{20}$ aryl, $C_7$-$C_{20}$ aralkyl, and $C_7$-$C_{20}$ alkaryl, wherein the composition does not form explosive crystals when stored at $-25°$ C. for 24 hours.

3. A composition according to claim 1, further comprising one or more conventional phlegmatisers (diluents).

4. A composition according to claim 1 wherein the active oxygen content attributable to the cyclic ketone peroxide is below 6 wt. %, based on the total weight of the cyclic ketone peroxide composition.

5. A composition according to claim 1 wherein the cyclic ketone peroxide is selected from the group consisting of cyclic ketone peroxides derived from acetone, methyl ethyl ketone, methyl propyl ketone, methyl isopropyl ketone, methyl butyl ketone, methyl isobutyl ketone, methyl amyl ketone, methyl isoamyl ketone, cyclohexanone, and mixtures thereof.

6. A composition according to claim 1, wherein $R_7$ and $R_8$ of the dialkyl peroxide according to formula $R_7$—O—O—$R_8$ (II) are independently selected from the group consisting of $C_4$-$C_{12}$ alkyl moieties.

7. A composition according to claim 1, wherein at least one of $R_7$ and $R_8$ of the dialkyl peroxide according to formula $R_7$—O—O—$R_8$ (II) is selected from the group consisting of branched $C_4$-$C_{12}$ alkyl moieties, preferably wherein both $R_7$ and $R_8$ of the dialkyl peroxide according to formula $R_7$—O—O—$R_8$ (II) are independently selected from the group consisting of branched $C_4$-$C_{12}$ alkyl moieties.

8. A composition according to claim 1, wherein the dialkyl peroxide according to formula $R_7$—O—O—$R_8$ (II) is di(tert-butyl) peroxide or di(tert-amyl) peroxide.

9. A cyclic ketone peroxide polymerization initiator composition comprising one or more cyclic ketone peroxides selected from a group of cyclic ketone peroxides derived from cyclopentanone, cyclohexanone, 2-methyl cyclohexanone, and 3,3,5-trimethyl cyclohexanone; and one or more dialkyl peroxides according to formula $R_7$—O—O—$R_8$ (II), wherein $R_7$ and $R_8$ are independently selected from the group consisting of substituted or unsubstituted, linear or branched $C_4$-$C_{20}$ alkyl, $C_3$-$C_{20}$ cycloalkyl, $C_6$-$C_{20}$ aryl, $C_7$-$C_{20}$ aralkyl, and $C_7$-$C_{20}$ alkaryl, and wherein the composition does not form explosive crystals when stored at $-25°$ C. for 24 hours.

10. The cyclic ketone peroxide polymerization initiator composition according to claim 1, wherein, after the storage at $-25°$ C. of 24 hours, explosive crystals are not formed upon the addition of seed crystals, and no growth of the seed crystals occurs following an additional 24 hours of storage at $-25°$ C.

11. The cyclic ketone peroxide polymerization initiator composition according to claim 1, wherein the composition is free of crystals following the addition of seed crystals and the additional 24 hours of storage at $-25°$ C.

12. The cyclic ketone peroxide polymerization initiator composition according to claim 2, wherein, after the storage at $-25°$ C. of 24 hours, explosive crystals are not formed upon the addition of seed crystals, and no growth of the seed crystals occurs following an additional 24 hours of storage at $-25°$ C.

13. The cyclic ketone peroxide polymerization initiator composition according to claim 12, wherein the composition is free of crystals following the addition of seed crystals and the additional 24 hours of storage at $-25°$ C.

14. The cyclic ketone peroxide polymerization initiator composition according to claim 9, wherein, after the storage at $-25°$ C. of 24 hours, explosive crystals are not formed upon the addition of seed crystals, and no growth of the seed crystals occurs following an additional 24 hours of storage at $-25°$ C.

15. The cyclic ketone peroxide polymerization initiator composition according to claim 14, wherein the composition is free of crystals following the addition of seed crystals and the additional 24 hours of storage at $-25°$ C.

* * * * *